(12) United States Patent
Li et al.

(10) Patent No.: US 12,409,221 B2
(45) Date of Patent: Sep. 9, 2025

(54) PHARMACEUTICAL PREPARATION FOR TREATING HEPATITIS B, PREPARATION METHOD THEREFOR AND USE THEREOF

(71) Applicant: GRAND THERAVAC LIFE SCIENCES (NANJING) CO., LTD., Nanjing (CN)

(72) Inventors: Jianqiang Li, Nanjing (CN); Jun Ge, Nanjing (CN); Sulin Ren, Nanjing (CN); Hongying Huang, Nanjing (CN); Jiaojiao Sun, Nanjing (CN); Honglin Sun, Nanjing (CN); Tong Zhou, Nanjing (CN); Yue Gu, Nanjing (CN); Xiaoxiao Chen, Nanjing (CN); Xue Zhou, Nanjing (CN)

(73) Assignee: Grand Theravac Life Sciences (Nanjing) Co., Ltd., Nanjing (CN)

( * ) Notice: Subject to any disclaimer, the term of this patent is extended or adjusted under 35 U.S.C. 154(b) by 913 days.

(21) Appl. No.: 17/418,131

(22) PCT Filed: Nov. 15, 2019

(86) PCT No.: PCT/CN2019/118778
§ 371 (c)(1),
(2) Date: Jun. 24, 2021

(87) PCT Pub. No.: WO2020/134682
PCT Pub. Date: Jul. 2, 2020

(65) Prior Publication Data
US 2022/0088188 A1   Mar. 24, 2022

(30) Foreign Application Priority Data
Dec. 24, 2018 (CN) .......... 201811580470.4

(51) Int. Cl.
*A61K 39/29* (2006.01)
*A61K 9/19* (2006.01)
(Continued)

(52) U.S. Cl.
CPC .............. *A61K 39/292* (2013.01); *A61K 9/19* (2013.01); *A61K 39/39* (2013.01); *A61K 47/26* (2013.01);
(Continued)

(58) Field of Classification Search
None
See application file for complete search history.

(56) References Cited

U.S. PATENT DOCUMENTS 9,878,035 B2    1/2018  Du et al.
2010/0330099 A1*  12/2010  Dagan ............... A61K 9/0019
                                                424/161.1
(Continued)

FOREIGN PATENT DOCUMENTS

CA   3059446 A1   10/2018
CN   1391482 A    1/2003
(Continued)

OTHER PUBLICATIONS

Machine translation of WO 2014/139359 by Du et al. Sep. 18, 2018.*
(Continued)

*Primary Examiner* — Shanon A. Foley
(74) *Attorney, Agent, or Firm* — CHRISTENSEN O'CONNOR JOHNSON KINDNESS PLLC

(57) ABSTRACT

The present invention discloses a pharmaceutical preparation for treating hepatitis B, a preparation method and use thereof. The pharmaceutical preparation comprises a solution of hepatitis B surface antigen, further a solution of hepatitis B core antigen, and furthermore an oligodeoxy-
(Continued)

Figure 1:
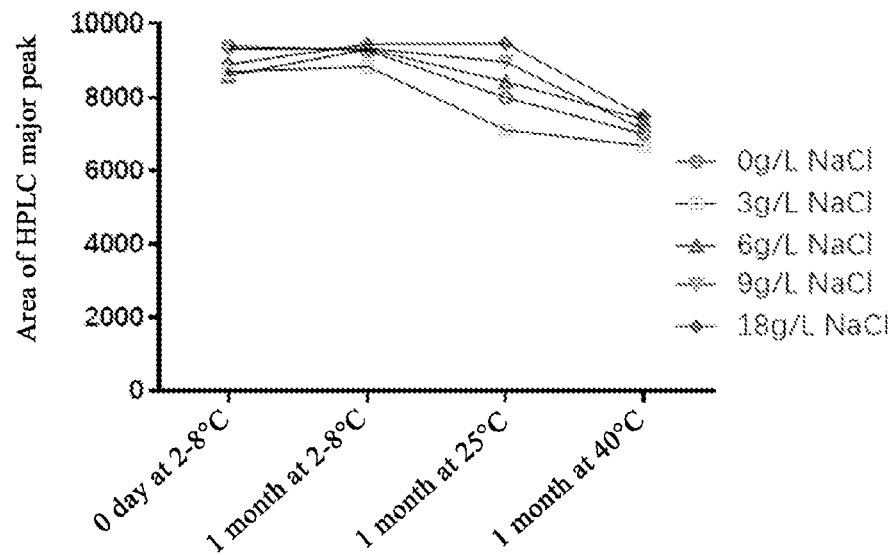

nucleotide solution. The pharmaceutical preparation is free of saccharide, has a simple composition and a good antigen stability, without the adverse reactions caused by aluminum adjuvants, and shows good preservation effects in long-term stability experiments.

19 Claims, 7 Drawing Sheets

Specification includes a Sequence Listing.

(51) Int. Cl.
*A61K 39/00* (2006.01)
*A61K 39/39* (2006.01)
*A61K 47/26* (2006.01)
*A61P 31/20* (2006.01)
*A61P 37/04* (2006.01)

(52) U.S. Cl.
CPC .............. *A61P 31/20* (2018.01); *A61P 37/04* (2018.01); *A61K 2039/575* (2013.01)

(56) References Cited

U.S. PATENT DOCUMENTS

| 2016/0324950 A1* | 11/2016 | Anderson | A61P 37/04 |
| 2021/0292419 A1 | 9/2021 | Burke et al. | |
| 2022/0088188 A1* | 3/2022 | Li | A61P 35/00 |

FOREIGN PATENT DOCUMENTS

| CN | 104043120 A | 9/2014 |
| CN | 108330145 A | 7/2018 |
| CN | 108659107 A | 10/2018 |
| EP | 2 974 740 A1 | 1/2016 |
| JP | 2009-503051 A | 1/2009 |
| JP | 213-530941 A | 8/2013 |
| JP | 2014-028831 A | 2/2014 |
| JP | 2014-506916 A | 3/2014 |
| JP | 2016-512204 A | 4/2016 |
| WO | 0041463 A2 | 7/2000 |
| WO | WO 00/41463 * | 7/2000 |
| WO | 2014/139539 A1 | 9/2014 |
| WO | WO 2014/139359 * | 9/2014 |
| WO | 2018195165 A1 | 10/2018 |

OTHER PUBLICATIONS

Sequence alignment of instant SEQ ID No. 1 with Geneseq db access No. BBM94286 in WO2014139359 Sep. 18, 2014.*
Sequence alignment of instant SEQ ID No. 2 with Geneseq db access No. BBM94286 in WO2014139359 Sep. 18, 2014.*
"Full Prescribing Information", provided by DYNAVAX™ for HEPLISAV-B®; 2017.*
Evans et al. (Journal of Pharmaceutical Sciences. Oct. 1, 2004; 93 (10):2458-75).*
Lobaina et al. (Molecular Immunology. 2005; 42: 289-294).*
Lewellyn et al. (Journal of Virology. 2011; 85 (3): 1298-1309).*
Jones et al. "Considerations for the use of polysorbates in biopharmaceuticals". Pharmaceutical Research. Aug. 2018; 35: 1-8.*
International Search Report mailed Mar. 5, 2020, issued in corresponding International Application No. PCT/CN2019/118778, filed Nov. 15, 2019, 12 pages.
Garidel, P., et al., "High-concentration protein formulations: How high is high?" European Journal of Pharmaceutics and Biopharmaceutics119:353-360, 2017.
"HEPLISAV-B Hepatitis B vaccine (recombinant), adjuvanted," <https://www.izsummitpartners.org/content/uploads/2018/03/Heplisav-B-monograph-with-Pl.pdf> [retrieved Aug. 17, 2022], p. 9, para. 11.
Extended European Search Report mailed Aug. 30, 2022, issued in corresponding European Application No. 19901730.2, filed Nov. 15, 2019, 9 pp.
Chinese Search Report dated Feb. 14, 2023, issue in corresponding Chinese Patent Application No. 2019112918854, filed Dec. 16, 2019, 5 pages.
Chen, Yi, "Asymmetric Vertical Flow Field-Flow Fractionation Technology Applied to the Study of Virus-Like Particles Stability," University of Chinese Academy of Sciences, Chinese Doctoral Dissertations Full-text Database, Doctoral e-Journal Publication Information: Year: 2016, Issue 12, Dec. 15, 2016, Abstract.
Search Report mailed Jul. 18, 2024, issued in corresponding Taiwanese Application No. 108141637, filed Dec. 24, 2018, 2 pages.
Chen, Yi., "Stability Investigation of Virus-like Particle by Asymmetrical Flow Field-Flow Fractionation" A Dissertation Submitted to the University of Chinese Academy of Sciences, Institute of Process Engineering, May 2016, 135 pages.
Office Action mailed Apr. 29, 2024, issued in Thai Application No. 2101003773 PCT, 6 pages.
Notice of Reasons for Refusal mailed Feb. 13, 2024, issued in corresponding Japanese Application No. 2021-536405, 7 pages.
Notice of Reasons for Refusal mailed Aug. 21, 2023, issued in corresponding Japanese Application No. 2021-536405, 14 pages.
Major, M, "Summary Basis for Regulatory Action: HEPLISAV-B," US. Food and Drug Administration, Nov. 9, 2017, 33 pages.
Decision on Rejection mailed Jan. 4, 2024, issued in corresponding Chinese Application No. 201911297005.4, filed Dec. 16, 2019, 16 pages.
First Office Action and Search Report mailed Feb. 15, 2023, issued in corresponding Chinese Application No. 201911297005.4, filed Dec. 16, 2019, 11 pages.
Second Office Action and Search Report mailed Jul. 31, 2023, issued in corresponding Chinese Application No. 201911297005.4, filed Dec. 16, 2019, 15 pages.
Chen, Yi., "Stability Investigation of Virus-like Particle by Asymmetrical Flow Field-Flow Fractionation" A Dissertation Submitted to the University of Chinese Academy of Sciences, Institute of Process Engineering, May 2016, English translation of abstract, 4 pages.

* cited by examiner

PHARMACEUTICAL PREPARATION FOR TREATING HEPATITIS B, PREPARATION METHOD THEREFOR AND USE THEREOF

The present application is a National Stage of International Application No. PCT/CN 2019/118778, filed Nov. 15, 2019, which claims priority to Chinese Patent Application No. 201811580470.4, filed Dec. 24, 2018, titled "Pharmaceutical preparation for treating hepatitis B, preparation method and use thereof", the disclosure of each of which is expressly incorporated herein by reference in its entirety.

TECHNICAL FIELD

The present invention belongs to the biomedicine field, and relates to a pharmaceutical preparation for treating hepatitis B, a preparation method and use thereof.

BACKGROUND TECHNOLOGY

Hepatitis B virus (HBV) infection is one of serious public health problems worldwide, and an important cause of chronic hepatitis B, cirrhosis and hepatocellular carcinoma (Fattovich G. J Hepatol 2008; 48: 335-352). Clinically, the common drugs for clinic treatment of chronic HBV infection mainly include nucleoside analogues and interferons. However, nucleoside analogs cannot completely remove cccDNA in liver cells, and their long-term use is liable to cause occurrence of drug-resistant mutants and rebound after drug discontinuance (Kwon H, Lok A S. Nat Rev Gastroenterol Hepatol 2011; 8: 275-284). Interferons are not suitable for asymptomatic HBV carriers. Among patients with chronic HBV, the HBeAg seroconversion rate after use for half a year is only 33%, and the interferons have higher side effects, which also limit their use (Tang S X, Yu G L. Lancet 1990; 335 (8684): 302).

At present, the widely used hepatitis B protein vaccines can produce protective neutralizing antibodies by inducing humoral immunity to achieve the goal of prevention. A large number of studies have shown that neutralizing antibodies can only eliminate the extracellular virus particles, and the elimination of intracellularly infective virus mainly relies on specific cellular immune response, helper T cells, and Th1-type cell factors producing from CD4+ T cells such as IFN-γ, in particular virus-specific cytotoxic T lymphocytes (CTL) (Chin R, Lacamini S. Rev Med Viorl, 2003: 13(4): 255-72). Whether the cellular immune response is strong will directly dominate the prognosis of hepatitis B. Therefore, an ideal therapeutic vaccine for hepatitis B is required to induce specific humoral and cellular immunity simultaneously, to break through the immune tolerance to hepatitis B.

CN104043120B provides a therapeutic vaccine for hepatitis B comprising a hepatitis B surface antigen (HBsAg), a hepatitis B core antigen (HBcAg), and an oligodeoxynucleotide (CpG), which can break through the immune tolerance to hepatitis B and is used for the treatment of viral hepatitis B, especially chronic hepatitis B.

Conventional hepatitis B vaccines usually contain aluminum hydroxide as an adjuvant, and aluminum adjuvants also enable antigens to be adsorbed thereon to reduce the interaction between antigen molecules, thereby increasing the antigen stability. However, aluminum adjuvants also have some disadvantages. For example, vaccination with an aluminum adjuvant may result in some adverse reactions such as erythema, subcutaneous nodules, contact hypersensitivity, granuloma, and myofascitis. Use of CpG adjuvants avoids the above-mentioned adverse effects of the aluminium hydroxide adjuvant. Meanwhile, it was unexpectedly found in the experiments that addition of saccharides, such as sucrose did not serve to protect the antigen, but reduced the antigen stability. Therefore, how to further improve the antigen stability of vaccine is a problem to be solved.

CONTENTS OF INVENTION

The present invention aims to further provide a pharmaceutical preparation for treating hepatitis B with a better antigen stability on the basis of the prior art. This pharmaceutical preparation has a good antigen stability and is suitable for large-scale production and use of a therapeutic vaccine for hepatitis B in the absence of aluminum adjuvants such as aluminum hydroxide and saccharides.

To achieve the above object, the present invention provides a pharmaceutical preparation for treating hepatitis B, comprising a solution of hepatitis B surface antigen, wherein the solution of hepatitis B surface antigen comprises a hepatitis B surface antigen or a fragment thereof and polysorbate 80.

Preferably, the solution of hepatitis B surface antigen further comprises a phosphate buffer agent.

Preferably, the pharmaceutical preparation further comprises a solution of hepatitis B core antigen, wherein the solution of hepatitis B core antigen comprises a hepatitis B core antigen or a fragment thereof, a phosphate buffer agent, and polysorbate 80.

More preferably, the pharmaceutical preparation further comprises an oligodeoxynucleotide solution, wherein the oligodeoxynucleotide solution comprises an oligodeoxynucleotide, a phosphate buffer agent, and polysorbate 80.

Preferably, the phosphate buffer agent comprises $Na_2HPO_4$ and $NaH_2PO_4$; more preferably, the phosphate buffer agent comprises $Na_2HPO_4$, $NaH_2PO_4$ and NaCl; further preferably, the weight ratio of $Na_2HPO_4$, $NaH_2PO_4$ and NaCl is 2:2.4:(6-18), preferably 2:2.4:(6-9), more preferably 2:2.4:9.

Preferably, polysorbate 80 has a concentration of from 0.03% (0.03 g/100 ml) to 0.1% (0.1 g/100 ml), preferably 0.05% (0.05 g/100 ml).

Further preferably, the pharmaceutical preparation is free of saccharides, such as sucrose.

Preferably, the amino acid sequence of hepatitis B surface antigen is shown in SEQ ID NO. 1; preferably, the amino acid sequence of hepatitis B core antigen is shown in SEQ ID NO. 2; preferably, the nucleotide sequence of oligodeoxynucleotide is one or more selected from the group consisting of SEQ ID NO. 3, SEQ ID NO. 4, SEQ ID NO. 5, SEQ ID NO. 6, SEQ ID NO. 7, SEQ ID NO. 8 and SEQ ID NO. 9, preferably SEQ ID NO. 3.

Preferably, the fragment of hepatitis B core antigen consists of 149-183 contiguous amino acids, preferably 152-183 contiguous amino acids in SEQ ID NO. 2.

The pharmaceutical preparation may be an injection preparation selected from an injection solution, a lyophilized powder for injection, or a sterile subpackaged preparation.

The present invention also provides a preparation method of the pharmaceutical preparation for treating hepatitis B, comprising the steps of:

1) adding water to dissolve a phosphate buffer agent to prepare a phosphate buffer solution, and adjusting the pH value to 7.0-7.4, preferably 7.2;
2) diluting polysorbate 80 with the phosphate buffer solution prepared in step 1) to prepare a polysorbate 80 solution;

3) adding a stock solution of hepatitis B surface antigen into the polysorbate 80 solution prepared in step 2) to prepare a solution of hepatitis B surface antigen;
4) adding a stock solution of hepatitis B core antigen into the polysorbate 80 solution prepared in step 2) to prepare a solution of hepatitis B core antigen;
5) dissolving an oligodeoxynucleotide in the phosphate buffer solution prepared in step 1) and diluting it to obtain a stock solution, and adding the polysorbate 80 solution prepared in step 2) to prepare an oligodeoxynucleotide solution; and
6) mixing the solution of hepatitis B surface antigen prepared in step 3), the solution of hepatitis B core antigen prepared in step 4) and the oligodeoxynucleotide solution prepared in step 5) to obtain the pharmaceutical preparation.

The present invention also provides use of the pharmaceutical preparation for treating hepatitis B or the pharmaceutical preparation prepared by the above-mentioned preparation method in the preparation of a medicament for treating a hepatitis B virus infection and/or a disease mediated by hepatitis B virus.

The hepatitis B virus infection and/or the disease mediated by hepatitis B virus is selected from hepatitis B, liver cirrhosis and liver cancer.

The present invention also provides use of the above-mentioned pharmaceutical preparation for treating hepatitis B or the pharmaceutical preparation prepared by the above-mentioned preparation method in the preparation of a medicament for producing humoral and cellular immune responses against hepatitis B virus in a subject.

The present invention also provides use of the above-mentioned pharmaceutical preparation for treating hepatitis B or the pharmaceutical preparation prepared by the above-mentioned preparation method in preparing a medicament for converting the subtype of hepatitis B core antibody in a subject.

Preferably, the above-mentioned medicament is a therapeutic vaccine.

The present invention also provides a method for treating a hepatitis B virus infection and/or a disease mediated by hepatitis B virus, comprising administering to a subject in need thereof a therapeutically effective amount of the above-mentioned pharmaceutical preparation for treating hepatitis B or the pharmaceutical preparation prepared by the above-mentioned preparation method; preferably, the hepatitis B virus infection and/or the disease mediated by hepatitis B virus is selected from hepatitis B, liver cirrhosis and liver cancer.

The present invention also provides a method for producing humoral and cellular immune responses against hepatitis B virus in a subject, comprising administering to a subject in need thereof a therapeutically effective amount of the above-mentioned pharmaceutical preparation for treating hepatitis B or a pharmaceutical preparation prepared by the above-mentioned preparation method.

The present invention also provides a method for converting the subtype of hepatitis B core antibody in a subject, comprising administering to a subject in need thereof a therapeutically effective amount of the above-mentioned pharmaceutical preparation for treating hepatitis B or a pharmaceutical preparation prepared by the above-mentioned preparation method.

Through extensive screening and research, the present inventors have determined that a phosphate buffer solution and polysorbate 80 as components can effective for maintaining antigen stability of a pharmaceutical preparation for a therapeutic vaccine for hepatitis B, and surprisingly the experiments have demonstrated that addition of saccharides, such as sucrose, to the antigen solution not only has no the protective effects of saccharides on the proteins, but also reduces the antigen stability. Therefore, the pharmaceutical preparation provided by the present invention has a simple composition and a good antigen stability in absence of saccharides and aluminum adjuvants, which exhibits good preservation effects in long-term stability experiments, can meet the requirements for vaccine production, storage and use, and is suitable for large-scale production and use of a therapeutic vaccine for hepatitis B.

DESCRIPTION OF DRAWINGS

The embodiments of the present invention will be described in detail below in conjunction with the accompanying drawings, wherein:

FIG. 1 shows the results of stability study for HBsAg preparations which comprise PBS buffer solutions with different concentrations of NaCl, standing at 2-8° C., 25° C. and 40° C. for 1 month;

FIG. 2 shows the results of stability study of HBsAg preparations standing at 40° C.;

FIG. 3 shows the results of stability study of HBsAg preparations standing at 2-8° C.;

FIG. 4 shows the HPLC profiles of HBsAg control preparation and a preparation comprising 0.05% TWEEN® 80 (polyoxythylene (20) sorbitan monooleate) after standing at 40° C.;

FIG. 5 shows the results of stability study of HBcAg preparations standing at 40° C.;

FIG. 6 shows the results of stability study of HBcAg preparations standing at 2-8° C.;

FIG. 7 shows the secretion levels of HBsAg antigen-specific IFN-γ for pharmaceutical preparations with various components stored separatedly after standing at 25° C.;

FIG. 8 shows the secretion levels of HBcAg antigen-specific IFN-γ for pharmaceutical preparations with various components stored separatedly after standing at 25° C.;

FIG. 9 shows the secretion levels of HBsAg antigen-specific IFN-γ for pharmaceutical preparations with various components stored separatedly after standing at 2-8° C.;

FIG. 10 shows the secretion levels of HBcAg antigen-specific IFN-γ for pharmaceutical preparations with various components stored separatedly after standing at 2-8° C.;

FIG. 11 shows the secretion levels of HBsAg antigen-specific IFN-γ for pharmaceutical preparations with various components stored mixedly after standing at 25° C.;

FIG. 12 shows the secretion levels of HBcAg antigen-specific IFN-γ for pharmaceutical preparations with various components stored mixedly after standing at 25° C.;

FIG. 13 shows the secretion levels of HBsAg antigen-specific IFN-γ for pharmaceutical preparations with various components stored mixedly after standing at 2-8° C.;

FIG. 14 shows the secretion levels of HBcAg antigen-specific IFN-γ for pharmaceutical preparations with various components stored mixedly after standing at 2-8° C.

SPECIFIC EMBODIMENTS

The present invention will be described in further detail below with reference to the specific embodiments. The examples given are only for the purpose of illustrating the present invention, and not intended to limit the scope of the present invention.

Example 1 Preparation of Various Components of Therapeutic Vaccine Preparation for Hepatitis B 1. Preparation of HBsAg Stock Solution:

The amino acid sequence of HBsAg protein is shown in SEQ ID NO. 1.

HBsAg protein was prepared from HBsAg gene recombinant yeast cells, and the types of yeast cells include *Hansenula*, *Saccharomyces* and *Pichia* yeasts, preferably *Hansenula* yeast.

Reference was made to Chinese patent application CN108330145A for the specific preparation procedure. HBsAg gene recombinant *Hansenula* yeast cells were fermented and cultured for harvesting cells. A HBsAg stock solution was prepared by cell disruption, and purification steps such as silica gel adsorption, column chromatography and TFF. The prepared HBsAg stock solution was required to have a purity of more than 95% and a protein content of not less than 200 μg/ml. Residual quantities of host DNA, host proteins and other chemical substances were all in compliance with the standards of Pharmacopoeia.

2. Preparation of HBcAg Stock Solution:

The amino acid sequence of HBcAg protein is shown in SEQ ID NO. 2.

HBcAg protein was prepared from HBcAg gene recombinant yeast cells, and the types of yeast cells include *Hansenula*, *Saccharomyces* and *Pichia* yeasts, preferably *Hansenula* yeast.

Reference was made Chinese patent application CN108047316A for the specific preparation procedure. HBcAg gene recombinant *Hansenula* cells were fermented and cultured for harvesting cells. A HBcAg stock solution was prepared by cell disruption, and purification steps such as ammonium sulfate treatment, column chromatography and TFF. The prepared HBcAg stock solution was required to have a purity of more than 95% and a protein content of not less than 200 μg/ml. Residual quantities of host DNA, host proteins and other chemical substances were all in compliance with the standards of Pharmacopoeia.

3. Preparation of Oligodeoxynucleotide (CpG):

As an oligodeoxynucleotide sequence fragment which was prepared synthetically, the oligodeoxynucleotide comprises one or more CpG motifs, preferably 18-25 nucleotides, which are fully thio-modified sequences, including:

```
                                         (SEQ ID NO. 3)
TCG TTC GTT CGT TCG TTC GTT, (SEQ ID NO. 4)
GTG CCA GCG TGC GCC ATG, (SEQ ID NO. 5)
TCG TCG TTT TGT CGT TTT GTC GTT, (SEQ ID NO. 6)
TGA CTG TGA ACG TTC GAG ATG A, (SEQ ID NO. 7)
TCG TTC GTT CGT TCG TTC GTT CGT T, (SEQ ID NO. 8)
TCG TCG TCG TCG TCG TCG TCG
or (SEQ ID NO. 9)
TCC ATG ACG TTC CTG ACG TT
and etc., preferably
                                         (SEQ ID NO. 3)
TCG TTC GTT CGT TCG TTC GTT.
```

Reference was made to Example 1 in Chinese patent CN104043120B for the specific preparation procedure. The synthesized CpG (SEQ ID NO. 3) was lyophilized into an active pharmaceutical ingredient of CpG as powder, which was required to have a purity of more than 90%, a water content of less than 15%, and a content of not less than 70%. Limit tests of heavy metal impurities and microorganisms were all in compliance with the standards of Pharmacopoeia.

Example 2 Preparation of Therapeutic Vaccine Preparation for Hepatitis B

1. PBS buffer solution: 2.0 g of $Na_2HPO_4 \cdot 12H_2O$, 2.4 g of $NaH_2PO_4 \cdot 2H_2O$, and 9 g of NaCl were dissolved and diluted to 1000 ml by adding water, followed by adjusting the pH value to 7.20 with hydrochloric acid or sodium hydroxide;
2. 0.5% polysorbate 80 (TWEEN® 80) solution: 5.0 g of TWEEN® 80 was weighed, and diluted to 1000 ml with the PBS buffer solution;
3. HBsAg solution: to the HBsAg stock solution (prepared in Example 1) was added 0.5% TWEEN® 80 solution, followed by diluting with the PBS buffer solution until the concentration of TWEEN® 80 reached 0.05%;
4. HBcAg solution: to the HBcAg stock solution (prepared in Example 1) was added 0.5% TWEEN® 80 solution, followed by diluting with the PBS buffer solution until the concentration of TWEEN® 80 reached 0.05%;
5. CpG solution: the CpG (prepared in Example 1) was dissolved and diluted with the PBS buffer solution to obtain a stock solution of CpG, which was then added with 0.5% TWEEN® 80 solution, followed by diluting with the PBS buffer solution until the concentration of TWEEN® 80 reached 0.05%;
6. A pharmaceutical preparation was obtained by mixing the HBsAg solution prepared in step 3, the HBcAg solution prepared in step 4, and the CpG solution prepared in step 5.

Example 3 Screening Test for Formulations of Therapeutic Vaccine Preparation for Hepatitis B Among the three components HBsAg, HBcAg and CpG, HBsAg is most susceptible to various factors, and has the poorest stability. Therefore, HBsAg was used as an index to screen the preparation formulations.

HBsAg mainly exists in the form of virus-like particles (hereinafter referred to as VLPs), and the area of major peak detected by HPLC represents the number of VLPs in the preparation. Thus, a decreased area of major peak represents a decreased amount of HBsAg in the form of VLP in the preparation.

1) Screening for Buffer Systems

Preparation of Solutions 1. 0.5% polysorbate 80 (TWEEN® 80) solution was prepared according to Example 2;
2. histidine buffer solution: 1.55 g of histidine and 2.095 g of histidine hydrochloride were dissolved by adding water and diluted to 1000 ml.
3. HBsAg solution (PBS buffer solution): to the HBsAg stock solution was added 0.5% TWEEN® 80 solution, followed by diluting with the PBS buffer solution until the concentration of TWEEN® 80 reached 0.05%.
4. HBsAg solution (histidine buffer solution): the HBsAg stock solution was dialyzed overnight through a semipermeable membrane and exchanged into a histidine buffer solution, 0.5% TWEEN® 80 solution was added, followed by diluting with the PBS buffer solution until the concentration of TWEEn® 80 reached 0.05%.

The above two HBsAg solutions were subjected to HPLC detection after standing at 40° C. for 1 month, and the results are shown in Table 1.

TABLE 1

Results of screening test for buffer systems for preparation

| Buffer system | Area of major peak at 0 month | Area of major peak at 1 month | |
|---|---|---|---|
| | | Standing at 2-8° C. | Standing at 40° C. |
| Histidine buffer solution | 5456.3 | 5033.0 | 3470.5 |
| PBS buffer solution | 10537.7 | 10164.6 | 9899.2 |

The test results of HPLC showed that the area of major peak of HBsAg solution prepared with the histidine buffer solution decreased by 36.4% after standing at 40° C. for 1 month, while the area of major peak of HBsAg solution prepared with the PBS buffer solution decreased only 6.1% after standing at 40° C. for 1 month. Therefore, PBS buffer solution was selected as the buffer system for the preparation.

2) Screening for PBS Buffer Solutions

PBS buffer solution was used for formulating the preparation, and the pH value was adjusted with hydrochloric acid or sodium hydroxide to 7.0-7.4, preferably 7.2.

NaCl was used to adjust the osmotic pressure of PBS buffer solution, and also protected HBsAg protein, so an experiment was conducted to screen an appropriate concentration of NaCl. In the PBS buffer solution, PB was a phosphate buffer pair, namely $Na_2HPO_4 \cdot 12H_2O$ and $NaH_2PO_4 \cdot 2H_2O$.

Preparation of solutions: the following groups of phosphate buffer agents (Table 2) were dissolved by adding water and diluted to 1000 ml respectively, to prepare PBS buffer solutions. The HBsAg stock solution was dialyzed overnight through a semipermeable membrane and exchanged into the following groups of PBS buffer solutions.

TABLE 2

Screening for conditions of PBS buffer solutions

| Component content (g) | PB+ 0 g/L NaCl | PB+ 3 g/L NaCl | PB+ 6 g/L NaCl | PB+ 9 g/L NaCl | PB+ 18 g/L NaCl |
|---|---|---|---|---|---|
| $Na_2HPO_4 \cdot 12H_2O$ | 2 | 2 | 2 | 2 | 2 |
| $NaH_2PO_4 \cdot 2H_2O$ | 2.4 | 2.4 | 2.4 | 2.4 | 2.4 |
| NaCl | 0 | 3 | 6 | 9 | 18 |

The above five HBsAg solutions were subjected to HPLC detection after standing at 2-8° C., 25° C. and 40° C. for 1 month, and the results are shown in FIG. 1.

The test results of HPLC showed that when the concentration of NaCl in the buffer solution was between 0-18 g/L, as NaCl concentration increased, the area of major peak for HBsAg solution decreased gradually by a decreased extent after standing for 1 month. There was no significant decrease of the areas of major peak for five HBsAg solutions after standing at 2-8° C. for 1 month; the areas of major peak for five HBsAg solutions decreased significantly by 13.9%-25.4% after standing at 40° C. for 1 month, and the area of major peak decreased gradually by a decreased extent as the concentration of NaCl increased; after standing at 25° C. for 1 month, the areas of major peak for NaCl concentrations of 0 g/L and 3 g/L significant decreased by 14.8% and 18.2% respectively, and the areas of major peak area decreased by less than 3.7% for NaCl concentrations of 6-18 g/L. Therefore, PB+6-18 g/L NaCl, preferably 6-9 g/L, further preferably 9 g/L was chosen as the buffer solution for the preparation.

3) Screening for Excipients

Preparation of Solutions:

1. 50% sucrose solution: 50 g of sucrose was weighed, and diluted with the PBS buffer solution to 100 ml;
2. HBsAg solution (TWEEN® 80): to the HBsAg stock solution was added 0.5% TWEEN® 80 solution, followed by diluting with the PBS buffer solution until the concentration of TWEEN® 80 reached 0.05%.
3. HBsAg solution (sucrose+TWEEN® 80): to the HBsAg stock solution were added 50% sucrose solution and 0.5% TWEEN® 80 solution, followed by diluting with the PBS buffer solution until the concentration of sucrose solution reached 5%, and the concentration of TWEEN® 80 reached 0.05%.

The above two HBsAg solutions were subjected to HPLC detection after standing at 40° C. for 1 month, and the results are shown in Table 3.

TABLE 3

Results of screening test for excipients of preparation

| Excipients of preparation | Area of major peak at 0 month | Area of major peak at 1 month | |
|---|---|---|---|
| | | Standing at 2-8° C. | Standing at 40° C. |
| Sucrose + TWEEN® 80 | 9938.6 | 9478.9 | 6801.3 |
| TWEEN® 80 | 10537.7 | 10164.6 | 9899.2 |

The test results of HPLC showed that the area of major peak of HBsAg preparation prepared with sucrose and TWEEN® 80 decreased by 31.6% after standing at 40° C. for 1 month, while the area of major peak of HBsAg preparation prepared with TWEEN® 80 alone decreased only by 6.1% after standing at 40° C. for 1 month. That is, sucrose did not function to protect the antigen, but reduced the antigen stability. Therefore, TWEEN® 80 was selected as an excipient of the preparation, which not only had a good antigen stability, but also may reduce the potential adverse reaction risks of complex components.

Example 4 Stability Test of Therapeutic Vaccine Preparation for Hepatitis B

1. The settings of experimental groups are shown in Table 4, Table 5 and Table 6, and the preparation method was the same as in Example 2.

TABLE 4

Screening for concentrations of Tween 80 in HBsAg solution

| Groups | HBsAg solution |
|---|---|
| Control preparation | free of TWEEN ® 80 |
| Formulation comprising 0.01% TWEEN ® 80 | 0.01% |
| Formulation comprising 0.03% TWEEN ® 80 | 0.03% |
| Formulation comprising 0.05% TWEEN ® 80 | 0.05% |
| Formulation comprising 0.1% TWEEN ® 80 | 0.1% |

TABLE 5

Screening for concentrations of Tween 80 in HBcAg solution

| Groups | HBcAg solution |
|---|---|
| Control preparation | free of TWEEN ® 80 |
| Formulation comprising 0.01% TWEEN ® 80 | 0.01% |
| Formulation comprising 0.03% TWEEN ® 80 | 0.03% |
| Formulation comprising 0.05% TWEEN ® 80 | 0.05% |
| Formulation comprising 0.1% TWEEN ® 80 | 0.1% |

TABLE 6

Screening for concentrations of Tween 80 in CpG solution

| Groups | CpG solution |
|---|---|
| Control preparation | free of TWEEN ® 80 |
| Formulation comprising 0.01% TWEEN ® 80 | 0.01% |
| Formulation comprising 0.03% TWEEN ® 80 | 0.03% |
| Formulation comprising 0.05% TWEEN ® 80 | 0.05% |
| Formulation comprising 0.1% TWEEN ® 80 | 0.1% |

2. Protocol of Stability Test

TABLE 7

Research design of preparation stability

| Conditions for stability test | 2-8° C. | 40° C. |
|---|---|---|
| Period of test | 6 months | 1 month |
| Sampling time point | 0, 1, 2, 3, 6 months | 0, 7, 15, 30 days |

Each sample for stability study was sampled at the specified sampling time points for HPLC detection.

3. Experimental Results

Figure 2:
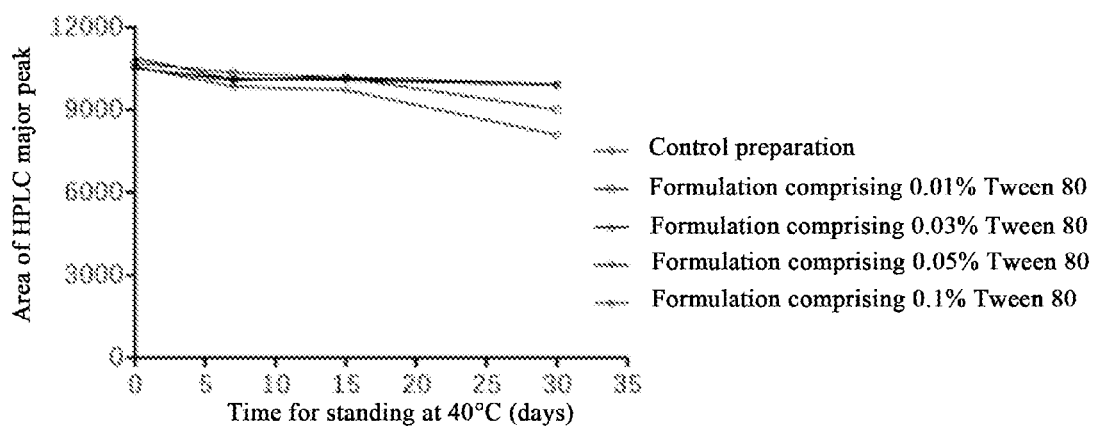
Figure 3:
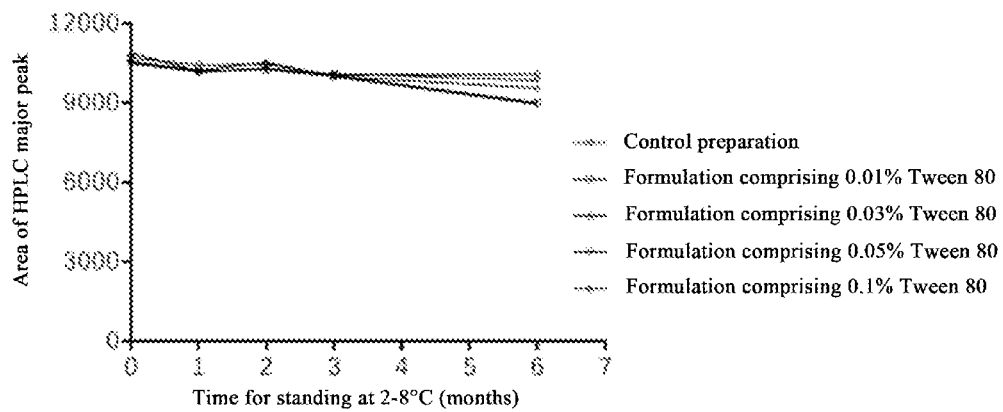

1) Analysis of Stability Results of HBsAg Preparations:

The HBsAg solutions of different formulations and HBsAg control preparation stood together at 40° C. and were sampled for detection on days 7, 15 and 30, respectively. The results showed that (see FIGS. 2 and 3): the area of HPLC major peak of HBsAg control preparation without TWEEN® 80 added decreased the fastest, and the area of major peak decreased by 23.5% after standing at 40° C. for 30 days; then, the solution in the formulation comprising 0.01% TWEEN® 80 decreased by 15.9%; the three solutions in the formulation comprising 0.03%-0.1% TWEEN® 80 showed substantially consistent decrease extent of about 6%.

The stability data for HBsAg solutions in different formulations and HBsAg control preparation standing together at 2-8° C. for 6 months were consistent with those standing at 40° C. Compared with the sample at zero time point, the areas of major peak of the control preparation (without TWEEN® 80 in the formulation) and the solutions containing 0.01%, 0.03%, 0.05%, and 0.1% TWEEN® 80 in the formulations at 6-month time point decreased by 15.4%, 15.8%, 12.2%, 6.5%, and 4.8%, respectively, indicating that TWEEN® 80 acted to protect HBsAg VLP.

Figure 4:
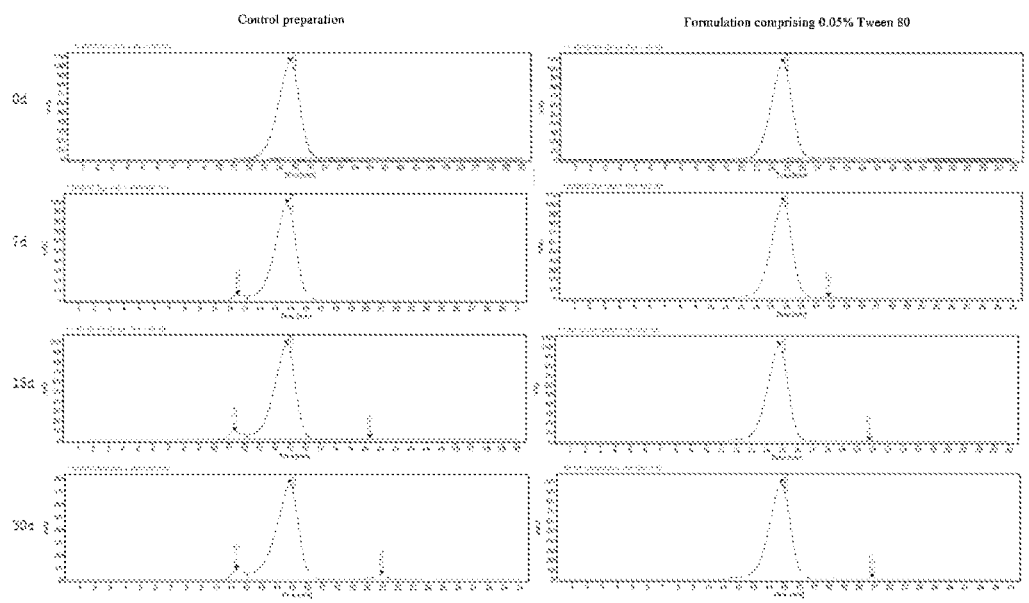

FIG. 4 showed that for the HBsAg control preparation an obvious aggregation peak appeared just after standing at 40° C. for 7 days, and the area of aggregation peak increased gradually as the standing time increased. However, for the preparation in the formulation comprising 0.05% TWEEN® 80, an obvious aggregation peak did not appear even after standing at 40° C. for 30 days. These indicated that TWEEN® 80 protected HBsAg VLPs by consistently maintaining their single VLP state and avoiding them from aggregation. Meanwhile, the formulation comprising 0.05% TWEEN® 80 was equivalent to that comprising 0.1% TWEEN® 80 in terms of effect, and the potential adverse reaction risks may also be reduced by reducing the amount of excipient.

2) Analysis of Stability Results of HBcAg Preparations:

Likewise, HBcAg mainly existed in the form of VLP, and the area of major peak detected by HPLC represented the number of VLPs in the preparation. Thus, a decreased area of major peak represented a decreased amount of HBcAg in the form of VLP in the preparation.

Figure 5:
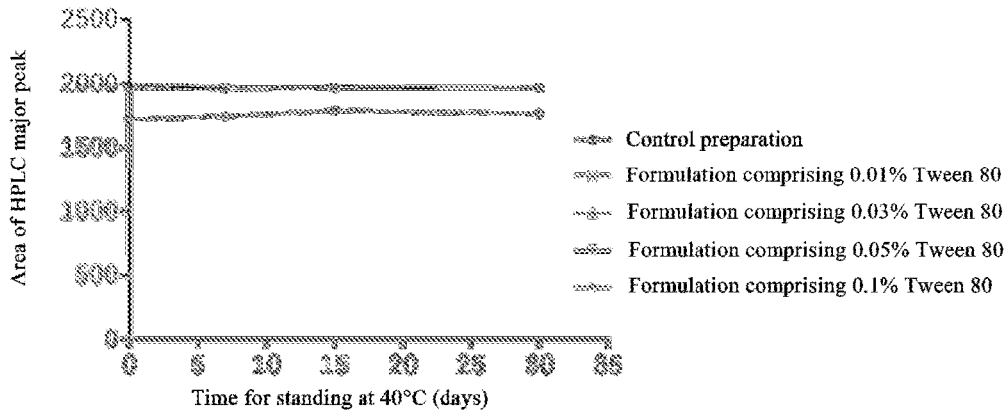
Figure 6:
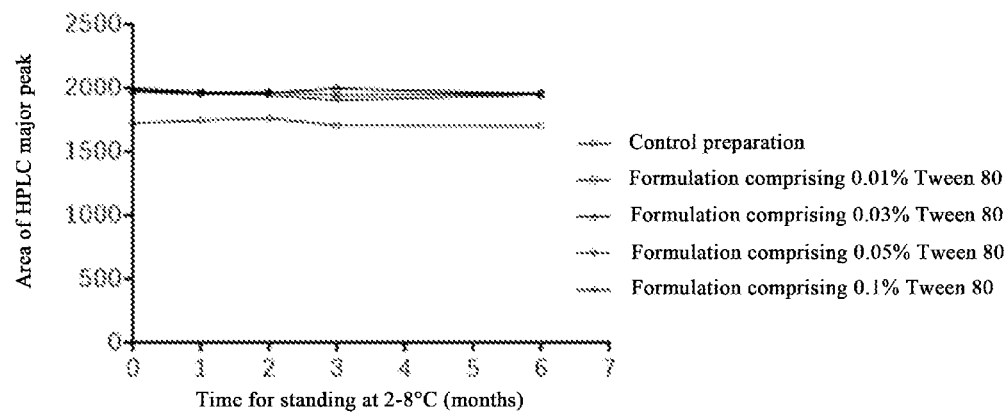

HPLC results (see FIGS. 5 and 6) showed that HBcAg VLPs were relatively stable, and there was no significant change in the areas of HPLC major peak after standing at 2-8° C. for 6 months and at 40° C. for 30 days.

3) Analysis of Stability Results of CpG Preparations:

Each sample for stability study was sampled at the specified sampling time points for detections of purity and relative activity.

The purity was detected by using a RP-UPLC method, the relative activity was detected by using a cytological method to characterize the binding activity of the CpG solution to human TLR9 receptors, and the result was denoted as a percentage ratio of the activity in relative to that of a reference substance (the CpG raw material prepared by the inventors was taken as the reference substance through sufficient structural characterization and content calibration, the relative activity value of which was defined as 100%).

The results of purity and relative activity showed (see Tables 8 and 9) that the CpG solutions were relatively stable with no significant changes in purity and relative activity after standing at 2-8° C. for 6 months and at 40° C. for 30 days.

TABLE 8

Research results of stability of CpG solutions after standing at 40° C.

| Content of Tween 80 (%) | Detection of CpG relative activity (%) | | | | Detection of CpG purity (%) | | | |
|---|---|---|---|---|---|---|---|---|
| | 0 d | 7 d | 15 d | 30 d | 0 d | 7 d | 15 d | 30 d |
| 0 | 99.0 | 104.2 | 98.9 | 93.3 | 94.83 | 95.11 | 95.85 | 95.33 |
| 0.01 | 104.4 | 103.7 | 100.5 | 96.1 | 94.84 | 95.09 | 95.36 | 95.4 |
| 0.03 | 104.9 | 100.9 | 106.6 | 85.2 | 95.25 | 95.03 | 95.16 | 95.31 |
| 0.05 | 103.1 | 105.9 | 105.4 | 93.5 | 95.25 | 95.97 | 95.51 | 95.37 |
| 0.1 | 103.9 | 103.7 | 98.8 | 96.1 | 96.07 | 95.95 | 95.27 | 95.28 |

TABLE 9

Research results of stability of CpG
solutions after standing at 2-8° C.

| Content of Tween 80 (%) | Detection of CpG relative activity (%) | | | | Detection of CpG purity (%) | | | |
|---|---|---|---|---|---|---|---|---|
| | 0 month | 1 month | 2 months | 3 months | 0 month | 1 month | 2 months | 3 months |
| 0 | 99.0 | 102.6 | 93.7 | 99.3 | 94.83 | 95.08 | 94.76 | 94.5 |
| 0.01 | 104.4 | 103.3 | 93.5 | 96.5 | 94.84 | 94.92 | 94.71 | 94.08 |
| 0.03 | 104.9 | 99.3 | 98.6 | 97.2 | 95.25 | 94.96 | 94.72 | 94.4 |
| 0.05 | 103.1 | 101.7 | 98.8 | 103.9 | 95.25 | 94.94 | 94.78 | 94.44 |
| 0.1 | 103.9 | 96.5 | 84.0 | 107.2 | 96.07 | 94.97 | 94.68 | 94.52 |

Example 5 Efficacy Test on Therapeutic Vaccine Preparation for Hepatitis B with Various Components Stored Separately 1. Laboratory animals: 80 female (n=8/group) C57BL/6 mice aged 5 weeks old were from Shanghai Lingchang Biotechnology Co., Ltd.

2. Setting of experimental groups: an HBsAg solution, an HBcAg solution and a CpG solution were prepared according to steps 1-5 of the preparation method described in Example 2 respectively, each being stored separately and sampled at the specified sampling time points (see Table 10); after sampling, the three components, i.e., the HBsAg solution, the HBcAg solution and the CpG solution were mixed according to step 6 in Example 2 to obtain a pharmaceutical preparation, which contains 50 μg/ml of HBsAg, 25 mg/ml of HBcAg, 25 μg/ml of CpG, and TWEEN® 80 at a concentration of 0.05%, respectively. Efficacy test was conducted on the pharmaceutical preparation.

TABLE 10

Efficacy test on therapeutic vaccine for hepatitis
B with various components stored separately

| Conditions for stability test | 25° C. | 2-8° C. |
|---|---|---|
| Period of test | 6 months | 12 months |
| Sampling time point | 0, 1, 2, 3, 6 months | 0, 3, 6, 9, 12 months |

3. Animal immunization: the mice were immunized once on day 0 by intramuscular injection at the leg in a vaccination volume of 200 μL per animal, and assessed for cellular immunity at day 7 post-immunization and for humoral immunity at day 28 post-immunization.

4. Cellular Immunity:

1) Detection procedure: the spleens were taken at day 7 post-immunization and the splenic lymphocytes were prepared by a conventional approach. Specifically, the spleens were taken aseptically, namely the spleens were cut with aseptic forceps and scissors, put into a 70 μm cell strainer, and placed into a plate containing 2 mL of pre-cooling treated 2% FBS (purchased from GIBCO Company)-PBS; the spleens were ground by using a grinding rod, so that the spleen cells entered into the plate through the mesh to obtain a cell suspension, and the suspension was placed into a 50 mL sterile centrifuge tube with a Pasteur pipette upon being filtered through a 40 μm cell strainer (purchased from BD Company) followed by centrifuging under 500×g at 4° C. for 5 min; the supernatant was discarded, the cells were re-suspended by adding 2 ml of 1× reagent for erythrocyte disruption (purchased from BD Company) and allowed to stand in the dark at 4° C. for 5 min for erythrocyte disruption; 10 mL of 2% FBS-PBS was added to stop the erythrocyte disruption reaction, followed by centrifuging under 500×g at 4° C. for 5 min and discarding the supernatant; 5 ml of 2% FBS-PBS was added to re-suspend the cells for further use. The splenocytes were stimulated with the stimulators HBsAg-specific peptide library PS4 and HBcAg-specific peptide library PCP, respectively; the secretion levels of IFN-γ specific for HBsAg and HBcAg antigens were detected by using an ELISPOT kit (BD Company) according to the instructions for the kit; the numbers of spots detected by the ELISPOT kit were read by using an ImmunoSPOT Series 3 enzyme-linked spot analyzer (see Example 7 in Chinese Patent CN104043120B for the specific procedure).

Reference was made to Example 7 in Chinese patent CN104043120B for HBsAg-specific peptide library PS4; and the sequences in HBcAg-specific peptide library PCP were shown in SEQ ID NOs. 10-24.

2) Assessment criteria: when the number of spots in the wells with serum-free culture medium ≤5 SFC, and the number of spots in the wells with sample ≥10 SFC, it was determined as positive; when 5 SFC<the number of spots in the wells with serum-free culture medium ≤10 SFC, and the number of spots in the wells with sample/the number of spots in the wells with serum-free culture medium ≥2, it was determined as positive; when the number of spots in the wells with serum-free culture medium >10 SFC, and the number of spots in the wells with sample/the number of spots in the wells with serum-free culture medium ≥3, it was determined as positive.

5. Humoral immunity:

1) Detection procedure: blood was collected at day 28 post-immunization, and serum was isolated (the whole blood was placed in a thermostatic incubator at 37° C. for 40 min, followed by centrifuging under 12,000 rpm at 4° C. for 10 min; and the supernatant was pipetted and frozen at −20° C. for further use). The positive conversion rates of HBsAb and HBcAb were detected by using an ELISA kit (Shanghai Kehua) according to the instructions for the kit. A blank control, a negative control and a sample to be detected were used for detection, and two parallel wells are used for each of them, wherein negative mouse serum was used as the negative control; to each well was added the negative control or the sample to be detected respectively except the blank control, and an enzyme conjugate was then added, followed by uniformly mixing, sealing the plate, and incubating at 37° C. for 30 min; each well was washed by using a washing solution, and to each well were added a developer A solution and a developer B solution, followed by uniformly mixing, sealing the plate, and incubating at 37° C. for 15 min; to each well was added a stop solution, followed by uniformly mixing; the OD value of each well at a wavelength of 450 nm was read by using a microplate reader.

2) Assessment criteria: as a reference value of HBsAb cut-off value (COV)=mean OD value of negative control× 2.1; when the OD value of the sample was smaller than the COV value, the detection result was determined as negative; when the OD value of the sample was greater than or equal to the COV value, the detection result was determined as positive.

As a reference value of HBcAb cut-off value (COV) =mean OD value of negative control×0.3; when the OD value of the sample was smaller than the COV value, the detection result was determined as positive; when the OD value of the sample was greater than or equal to the COV value, the detection result was determined as negative.

6. Experimental Results
1) Conditions for Stability Test at 25° C.:

TABLE 11

Efficacy results of pharmaceutical preparations under the conditions for stability test at 25° C.

| Storage time/month | Total number | Cellular immunity | | Humoral immunity | |
| --- | --- | --- | --- | --- | --- |
| | | Positive rate of HBsAg % | Positive rate of HBcAg % | Positive conversion rate of HBsAb % | Positive conversion rate of HBcAb % |
| 0 | 8 | 100 | 100 | 100 | 62.5 |
| 1 | 8 | 100 | 100 | 62.5 | 100 |
| 2 | 8 | 100 | 100 | 100 | 100 |
| 3 | 8 | 100 | 100 | 75 | 100 |
| 6 | 8 | 100 | 100 | 100 | 100 |

Result Analysis

Figure 7:
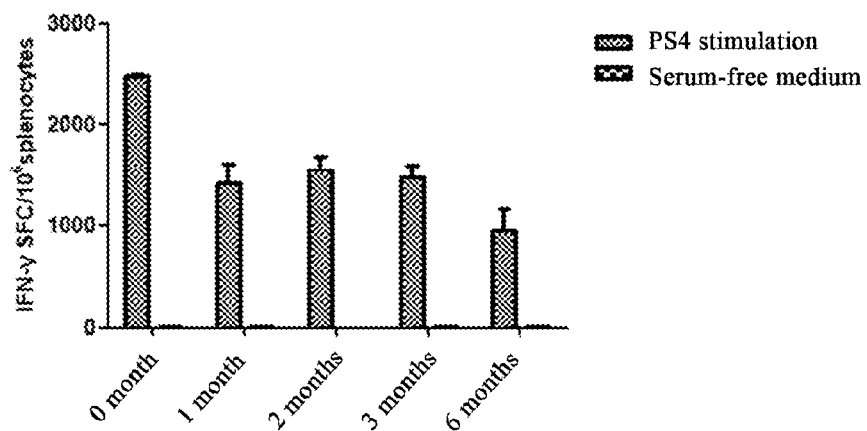
Figure 8:
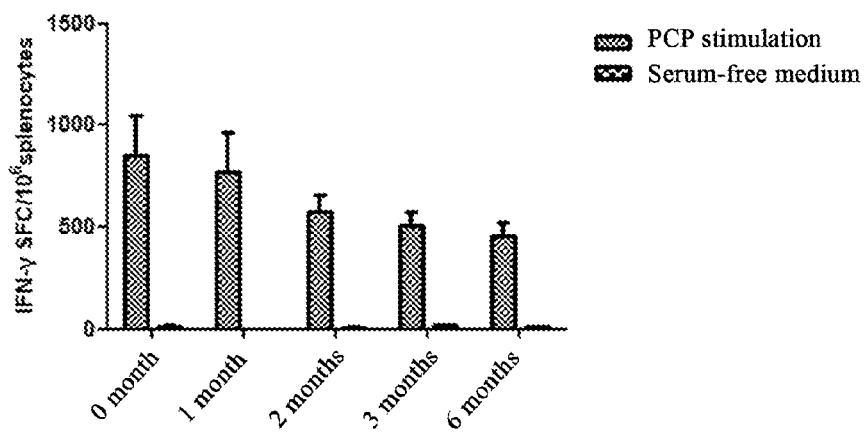

Detection results of cell immunity level: the results of ELISPOT spot were shown in FIGS. 7 and 8, indicating that during 0-6 months, the positive conversion rates for all IFN-γ specific for HBsAg and IFN-γ specific for HBcAg were 100%, all of which were higher than 70%, and the results of cellular immunity test were qualified. Detection results of humoral immunity level showed that the positive conversion rates of both HBsAb and HBcAb were above 62.5%, all of which were higher than 50%, and the results of humoral immunity test were qualified.

2) Conditions for Stability Test at 2-8° C.:

TABLE 12

Efficacy results of pharmaceutical preparations under the conditions for stability test at 2-8° C.

| Storage time/month | Total number | Cellular immunity | | Humoral immunity | |
| --- | --- | --- | --- | --- | --- |
| | | Positive rate of HBsAg % | Positive rate of HBcAg % | Positive conversion rate of HBsAb % | Positive conversion rate of HBcAb % |
| 0 | 8 | 100 | 100 | 100 | 62.5 |
| 3 | 8 | 100 | 87.5 | 75 | 100 |
| 6 | 8 | 100 | 100 | 75 | 100 |
| 9 | 8 | 100 | 100 | 100 | 100 |
| 12 | 8 | 100 | 100 | 75 | 100 |

Result Analysis

Figure 9:
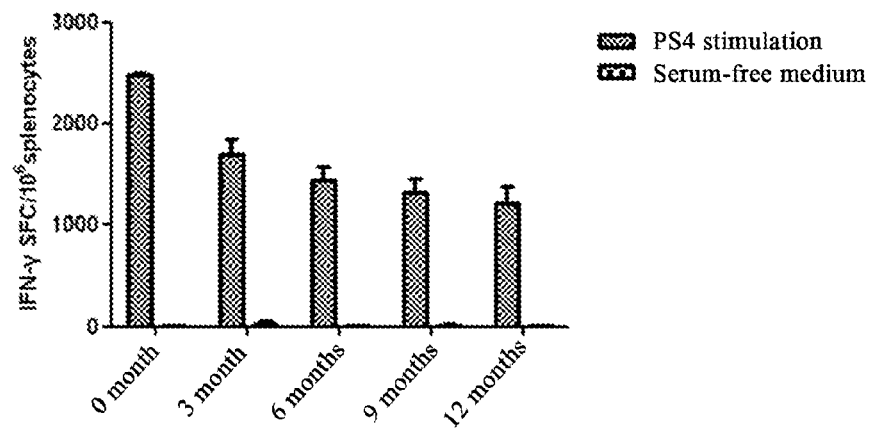
Figure 10:
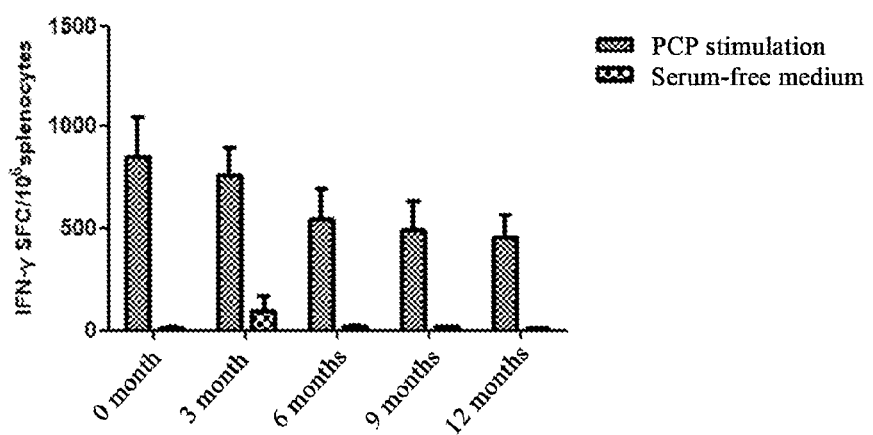

Detection results of cell immunity level: the results of ELISPOT spot were shown in FIGS. 9 and 10, indicating that during 0-12 months, the positive conversion rates of all IFN-γ specific for HBsAg were 100% and the positive conversion rates of IFN-γ specific for HBcAg were higher than 87.5%, all of which were higher than 70%, and the results of cellular immunity test were qualified. The detection results of humoral immunity level showed that the positive conversion rates of both HBsAb and HBcAb were above 62.5%, all of which were higher than 50%, and the results of humoral immunity test were qualified.

Example 6 Efficacy Test on Therapeutic Vaccine Preparation for Hepatitis B with Various Components Stored Mixedly 1. Laboratory animals: 64 female (n=8/group) C57BL/6 mice aged 5 weeks old were from Shanghai Lingchang Biotechnology Co., Ltd.

2. Setting of experimental group: the pharmaceutical preparation was prepared according to the preparation method in Example 2, which comprises 50 μg/ml of HBsAg, 25 μg/ml of HBcAg, 200 μg/ml of CpG, and TWEEN® 80 at a concentration of 0.05%, respectively. After standing for storage, the pharmaceutical preparation was sampled at the defined sampling time points (see Table 13) for efficacy test.

TABLE 13

Efficacy test on therapeutic vaccine for hepatitis B with various components stored mixedly

| Conditions for stability test | 25° C. | 2-8° C. |
|---|---|---|
| Period of test | 3 months | 6 months |
| Sampling time point | 0, 1, 2, 3 months | 0, 1, 3, 6 months |

3. Animal immunization: the mice were immunized once on day 0 by intramuscular injection into the leg in a vaccination volume of 200 μL per animal, and assessed for cellular immunity level at day 7 post-immunization and for humoral immunity level at day 28 post-immunization.

4. Cellular immunity: the detection procedure and assessment criteria were the same as in Example 5.

5. Humoral immunity: the detection procedure and assessment criteria were the same as in Example 5.

6. Experimental Results

1) Conditions for Stability Test at 25° C.:

TABLE 14

Efficacy results of pharmaceutical preparations under the conditions for stability test at 25° C.

| | | Cellular immunity | | Humoral immunity | |
|---|---|---|---|---|---|
| Storage time/month | Total number | Positive rate of HBsAg % | Positive rate of HBcAg % | positive conversion rate of HBsAb % | positive conversion rate of HBcAb % |
| 0 | 8 | 100 | 100 | 62.5 | 100 |
| 1 | 8 | 100 | 75 | 75 | 100 |
| 2 | 8 | 100 | 75 | 75 | 75 |
| 3 | 8 | 100 | 75 | 75 | 100 |

Figure 11:
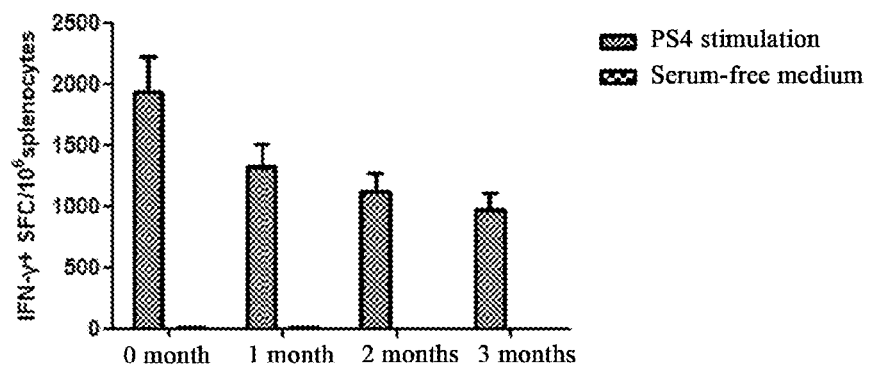
Figure 12:
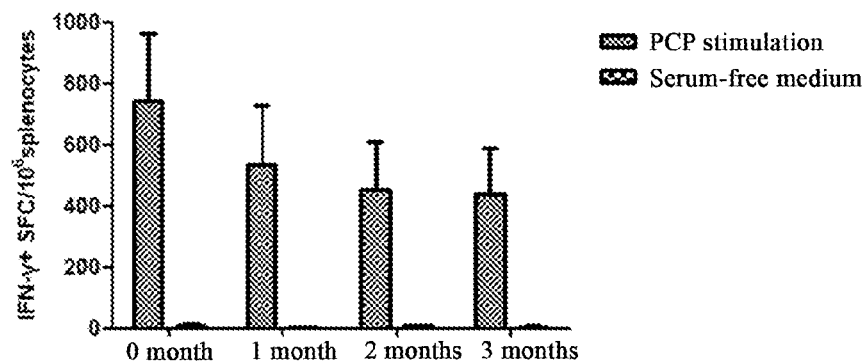

Result Analysis:

The detection results of cell immunity level: the results of ELISPOT spot were shown in FIGS. 11 and 12, indicating that during 0-3 months, the positive conversion rates for all IFN-γ specific for HBsAg were 100%, and the positive conversion rates for IFN-γ specific for HBcAg were higher than 75%, all of which were higher than 70%, and the results of cellular immunity test were qualified. Detection results of humoral immunity level showed that the positive conversion rates for both HBsAb and HBcAb were above 62.5%, all of which were higher than 50%, and the results of humoral immunity test were qualified.

2) Conditions for Stability Test at 2-8° C.:

TABLE 15

Efficacy results of pharmaceutical preparations under the conditions for stability test at 2-8° C.

| | | Cellular immunity | | Humoral immunity | |
|---|---|---|---|---|---|
| Storage time/month | Total number | Positive rate of HBsAg % | Positive rate of HBcAg % | Positive conversion rate of HBsAb % | Positive conversion rate of HBcAb % |
| 0 | 8 | 100 | 100 | 62.5 | 100 |
| 1 | 8 | 100 | 100 | 62.5 | 100 |
| 3 | 8 | 100 | 100 | 75 | 100 |
| 6 | 8 | 100 | 100 | 75 | 100 |

Figure 13:
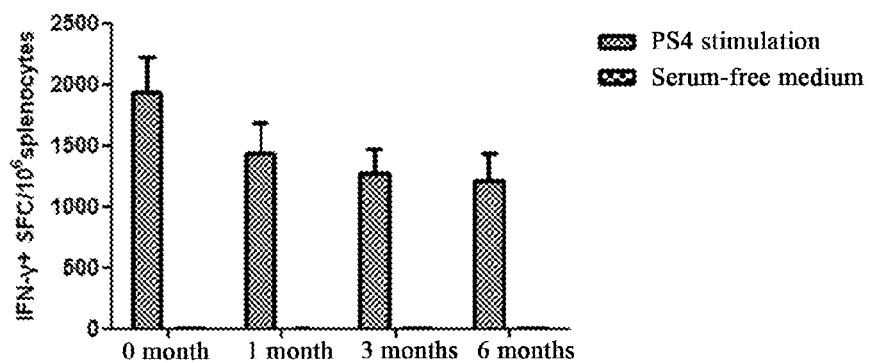
Figure 14:
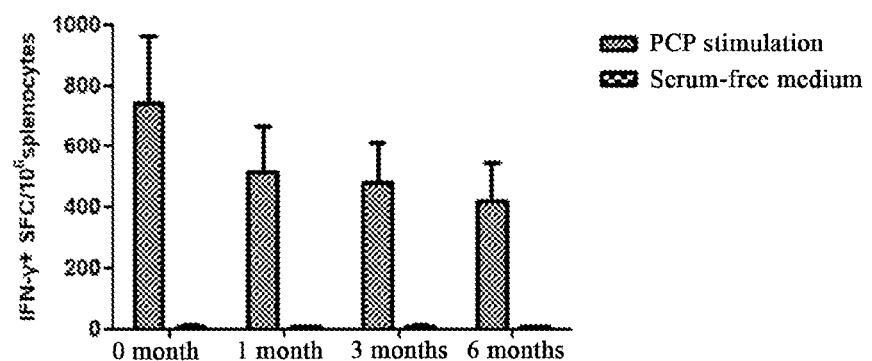

Result Analysis:

The detection results for cell immunity level: the results of ELISPOT spot were shown in FIGS. 13 and 14, indicating that during 0-6 months, the positive conversion rates for all IFN-γ specific for HBsAg was 100%, and the positive conversion rates for all IFN-γ specific for HBcAg were 100%, all of which were higher than 70%, and the results of cellular immunity test were qualified. The detection results for humoral immunity level showed that the positive conversion rates for both HBsAb and HBcAb were above 62.5%, all of which were higher than 50%, and the results of humoral immunity test were qualified.

In summary, the pharmaceutical preparation for treating hepatitis B provided by the present invention is free of saccharide, and avoids the adverse reactions caused by the aluminum hydroxide adjuvant by using a CpG adjuvant. Meanwhile, by adding appropriate amounts of polysorbate 80 and phosphate buffer agent, it enables the entire formulation to have a simple composition and shows a good antigen stability. This pharmaceutical preparation exhibits good preservation effects in long-term stability experiments, meets the requirements of vaccine production, storage and use, is suitable for large-scale production and use of therapeutic vaccine for hepatitis B, and has a wide market prospect.

Although the present invention has been described in detail above, those skilled in the art understand that various modifications and changes can be made to the present invention without departing from the spirit and scope of the present invention. It is intended that the scope of the claims of the present invention is not limited to the detailed description set forth above, and the modifications and changes shall fall within the scope of the claims.

The invention claimed is:

1. A pharmaceutical preparation for treating hepatitis B, comprising a solution of hepatitis B surface antigen, a solution of hepatitis B core antigen and an oligodeoxynucleotide solution, wherein the solution of hepatitis B surface antigen comprises a hepatitis B surface antigen or a fragment thereof, a phosphate buffer agent, and polysorbate 80, wherein the solution of hepatitis B core antigen comprises a hepatitis B core antigen or a fragment thereof, a phosphate buffer agent, and polysorbate 80, and wherein the oligodeoxynucleotide solution comprises an oligodeoxynucleotide, a phosphate buffer agent, and polysorbate 80, wherein the concentration of polysorbate 80 is from 0.03 g/100 mL to 0.1 g/100 mL.

2. The pharmaceutical preparation of claim 1, wherein the concentration of polysorbate 80 is 0.05 g/100 ml.

3. The pharmaceutical preparation of claim 1, wherein the phosphate buffer agent comprises $Na_2HPO_4$ and $NaH_2PO_4$.

4. The pharmaceutical preparation of claim 3, wherein the phosphate buffer agent comprises $Na_2HPO_4$, $NaH_2PO_4$ and NaCl.

5. The pharmaceutical preparation of claim 4, wherein the weight ratio of $Na_2HPO_4$, $NaH_2PO_4$ and NaCl is 2:2.4:(6-18).

6. The pharmaceutical preparation of claim 5, wherein the weight ratio of $Na_2HPO_4$, $NaH_2PO_4$ and NaCl is 2:2.4:(6-9).

7. The pharmaceutical preparation of claim 6, wherein the weight ratio of $Na_2HPO_4$, $NaH_2PO_4$ and NaCl is 2:2.4:9.

8. The pharmaceutical preparation of claim 1, wherein the pharmaceutical preparation is free of saccharide.

9. The pharmaceutical preparation of claim 1, wherein the amino acid sequence of hepatitis B surface antigen is SEQ ID NO. 1; the amino acid sequence of hepatitis B core antigen is SEQ ID NO. 2; and the nucleotide sequence of oligodeoxynucleotide is one or more selected from the group consisting of SEQ ID NO. 3, SEQ ID NO. 4, SEQ ID NO. 5, SEQ ID NO. 6, SEQ ID NO. 7, SEQ ID NO. 8 and SEQ ID NO. 9.

10. The pharmaceutical preparation of claim 9, wherein the fragment of hepatitis B core antigen consists of 149-183 contiguous amino acids in SEQ ID NO. 2.

11. The pharmaceutical preparation of claim 10, wherein the fragment of hepatitis B core antigen consists of 152-183 contiguous amino acids in SEQ ID NO. 2.

12. The pharmaceutical preparation of claim 9, wherein the nucleotide sequence of oligodeoxynucleotide is SEQ ID NO. 3.

13. The pharmaceutical preparation of claim 1, wherein the pharmaceutical preparation is an injection preparation selected from an injection solution, a lyophilized powder for injection or a sterile subpackaged preparation.

14. A method for treating a hepatitis B virus infection and/or a disease mediated by hepatitis B virus, comprising administering to a subject in need thereof a therapeutically effective amount of the pharmaceutical preparation of claim 1.

15. The method of claim 14, wherein the hepatitis B virus infection and/or the disease mediated by hepatitis B virus is selected from hepatitis B, liver cirrhosis and liver cancer.

16. A method for producing humoral and cellular immune responses against hepatitis B virus in a subject, comprising administering to a subject in need thereof a therapeutically effective amount of the pharmaceutical preparation of claim 1.

17. A method for converting the subtype of hepatitis B core antibody in a subject, comprising administering to a subject in need thereof a therapeutically effective amount of the pharmaceutical preparation of claim 1.

18. A method for preparing the pharmaceutical preparation of claim 1, comprising the steps of:
   1) Adding water to dissolve the phosphate buffer agent to prepare a phosphate buffer solution, and adjusting the pH value to 7.0-7.4;
   2) diluting polysorbate 80 with the phosphate buffer solution prepared in step 1) to prepare a polysorbate 80 solution;
   3) adding a stock solution of hepatitis B surface antigen into the polysorbate 80 solution prepared in step 2) to prepare a solution of hepatitis B surface antigen;
   4) adding a stock solution of hepatitis B core antigen into the polysorbate 80 solution prepared in step 2) to prepare a solution of hepatitis B core antigen;
   5) Dissolving an oligodeoxynucleotide in the phosphate buffer solution prepared in step 1) and diluting it to form a stock solution, and adding the polysorbate 80 solution prepared in step 2) to prepare an oligodeoxynucleotide solution; and
   6) mixing the solution of hepatitis B surface antigen prepared in step 3), the solution of hepatitis B core antigen prepared in step 4) and the oligodeoxynucleotide solution prepared in step 5) to obtain the pharmaceutical preparation.

19. The method of claim 18, wherein adjusting the pH is adjusted to 7.2 in step 1.

* * * * *

SEQUENCE LISTING

<160> NUMBER OF SEQ ID NOS: 24

<210> SEQ ID NO 1
<211> LENGTH: 226
<212> TYPE: PRT
<213> ORGANISM: Artificial Sequence
<220> FEATURE:
<223> OTHER INFORMATION: Synthetic

<400> SEQUENCE: 1

```
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

Tyr Ile
225
```

<210> SEQ ID NO 2
<211> LENGTH: 183
<212> TYPE: PRT
<213> ORGANISM: Artificial Sequence
<220> FEATURE:
<223> OTHER INFORMATION: Synthetic

<400> SEQUENCE: 2

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60
```

```
Leu Met Asn Leu Ala Thr Trp Val Gly Ser Asn Leu Glu Asp Pro Ala
 65                  70                  75                  80

Ser Arg Glu Leu Val Val Ser Tyr Val Asn Val Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Asn Ala Pro Ile Leu Ser Thr Leu Pro
    130                 135                 140

Glu Thr Thr Val Val Arg Arg Gly Arg Ser Pro Arg Arg Thr
145                 150                 155                 160

Pro Ser Pro Arg Arg Arg Ser Gln Ser Pro Arg Arg Arg Ser
            165                 170                 175

Gln Ser Arg Glu Ser Gln Cys
        180
```

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
tcgttcgttc gttcgttcgt t                                      21

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
gtgccagcgt gcgccatg                                          18

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
tcgtcgtttt gtcgttttgt cgtt                                   24

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
tgactgtgaa cgttcgagat ga                                     22

<210> SEQ ID NO 7
<211> LENGTH: 25
<212> TYPE: DNA
<213> ORGANISM: Artificial Sequence
<220> FEATURE:
<223> OTHER INFORMATION: Synthetic -continued

<400> SEQUENCE: 7
tcgttcgttc gttcgttcgt tcgtt                                            25

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
tcgtcgtcgt cgtcgtcgtc g                                                21

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tccatgacgt tcctgacgtt                                                  20

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Ser Pro His His Thr Ala Leu Arg Gln Ala Ile Leu Cys Trp Gly
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Thr Ala Leu Arg Gln Ala Ile Leu Cys Trp Gly Glu Leu Met Asn
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic

<400> SEQUENCE: 12

Gln Ala Ile Leu Cys Trp Gly Glu Leu Met Asn Leu Ala Thr Trp
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic

<400> SEQUENCE: 13

Cys Trp Gly Glu Leu Met Asn Leu Ala Thr Trp Val Gly Ser Asn

```
<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Leu Met Asn Leu Ala Thr Trp Val Gly Ser Asn Leu Glu Asp Pro
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic

<400> SEQUENCE: 15

Ala Thr Trp Val Gly Ser Asn Leu Glu Asp Pro Ala Ser Arg Glu
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Gly Ser Asn Leu Glu Asp Pro Ala Ser Arg Glu Leu Val Val Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic

<400> SEQUENCE: 17

Glu Asp Pro Ala Ser Arg Glu Leu Val Val Ser Tyr Val Asn Val
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Ser Arg Glu Leu Val Val Ser Tyr Val Asn Val Asn Met Gly Leu
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic

<400> SEQUENCE: 19

Val Val Ser Tyr Val Asn Val Asn Met Gly Leu Lys Ile Arg Gln
1               5                   10                  15
```

```
<210> SEQ ID NO 20
<211> LENGTH: 15
<212> TYPE: PRT
<213> ORGANISM: Artificial Sequence
<220> FEATURE:
<223> OTHER INFORMATION: Synthetic

<400> SEQUENCE: 20

Val Asn Val Asn Met Gly Leu Lys Ile Arg Gln Leu Leu Trp Phe
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic

<400> SEQUENCE: 21

Met Gly Leu Lys Ile Arg Gln Leu Leu Trp Phe His Ile Ser Cys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic

<400> SEQUENCE: 22

Ile Arg Gln Leu Leu Trp Phe His Ile Ser Cys Leu Thr Phe Gly
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Leu Trp Phe His Ile Ser Cys Leu Thr Phe Gly Arg Glu Thr Val
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Ile Ser Cys Leu Thr Phe Gly Arg Glu Thr Val Leu Glu Tyr Leu
1               5                   10                  15
```